United States Patent
Siccardi et al.

(10) Patent No.: US 11,141,173 B2
(45) Date of Patent: Oct. 12, 2021

(54) GUIDE FOR FLEXIBLE BONE DRILL AND BONE RESECTION INSTRUMENT

(71) Applicant: MEDACTA INTERNATIONAL S.A., Castel San Pietro (CH)

(72) Inventors: Francesco Siccardi, Castel San Pietro (CH); Sascha Berberich, Castel San Pietro (CH); Ernst Kehrli, Castel San Pietro (CH); Matteo Ponzoni, Castel San Pietro (CH); Riccardo Lucchini, Castel San Pietro (CH); Gianluca Parisi, Castel San Pietro (CH); Matteo Ferrari, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 135 days.

(21) Appl. No.: 16/475,015

(22) PCT Filed: Dec. 20, 2017

(86) PCT No.: PCT/IB2017/058191
§ 371 (c)(1),
(2) Date: Jun. 28, 2019

(87) PCT Pub. No.: WO2018/122687
PCT Pub. Date: Jul. 5, 2018

(65) Prior Publication Data
US 2020/0000481 A1    Jan. 2, 2020

(30) Foreign Application Priority Data

Dec. 29, 2016   (IT) .................... 102016000132039

(51) Int. Cl.
*A61B 17/17*   (2006.01)
*A61B 17/16*   (2006.01)
(Continued)

(52) U.S. Cl.
CPC .......... *A61B 17/17* (2013.01); *A61B 17/1631* (2013.01); *A61B 17/1604* (2013.01);
(Continued)

(58) Field of Classification Search
CPC ............ A61B 17/1742; A61B 17/1778; A61B 17/1633; A61B 17/1644; A61B 17/1684;
(Continued)

(56) References Cited

U.S. PATENT DOCUMENTS 5,895,389 A   4/1999  Schenk et al.
6,068,642 A   5/2000  Johnson et al.
(Continued)

OTHER PUBLICATIONS

International Search Report for PCT/IB2017/058191, dated Apr. 17, 2018, 3 pages.

*Primary Examiner* — Marcela I. Shirsat
(74) *Attorney, Agent, or Firm* — Meunier Carlin & Curfman LLC

(57) ABSTRACT

Disclosed is a guide for a flexible bone drill, including: a first body provided internally with a through channel; a second, internally hollow body, into which said first body can be inserted; said second body being provided with a through hole suitable to be placed in fluidic connection with the internal through channel of said first body; and said second body and said first body sliding relative to one another to vary the relative position of the hole with respect to said through channel. Other aspects are described and claimed.

20 Claims, 7 Drawing Sheets

(51) Int. Cl.
*A61B 90/00* (2016.01)
*A61B 17/00* (2006.01)

(52) U.S. Cl.
CPC ....... *A61B 17/1615* (2013.01); *A61B 17/1617* (2013.01); *A61B 17/1622* (2013.01); *A61B 17/1633* (2013.01); *A61B 17/1664* (2013.01); *A61B 17/1666* (2013.01); *A61B 17/1684* (2013.01); *A61B 17/1739* (2013.01); *A61B 17/1742* (2013.01); *A61B 17/1778* (2016.11); *A61B 2017/00477* (2013.01); *A61B 2090/035* (2016.02)

(58) Field of Classification Search
CPC ............ A61B 17/1631; A61B 17/1615; A61B 17/1604; A61B 17/1666; A61B 17/1739; A61B 17/1622; A61B 17/1617; A61B 2017/00477; A61B 17/1664; A61F 2/4601; A61F 2/4607
USPC .......................................... 606/79–85, 96–98
See application file for complete search history.

(56) References Cited

U.S. PATENT DOCUMENTS

| | | |
|---|---|---|
| 2008/0114365 A1 | 5/2008 | Sasing et al. |
| 2013/0110112 A1* | 5/2013 | Lehenkari .......... A61B 17/1617 606/80 |
| 2014/0309641 A1* | 10/2014 | Bourque ................ A61B 17/16 606/80 |

* cited by examiner

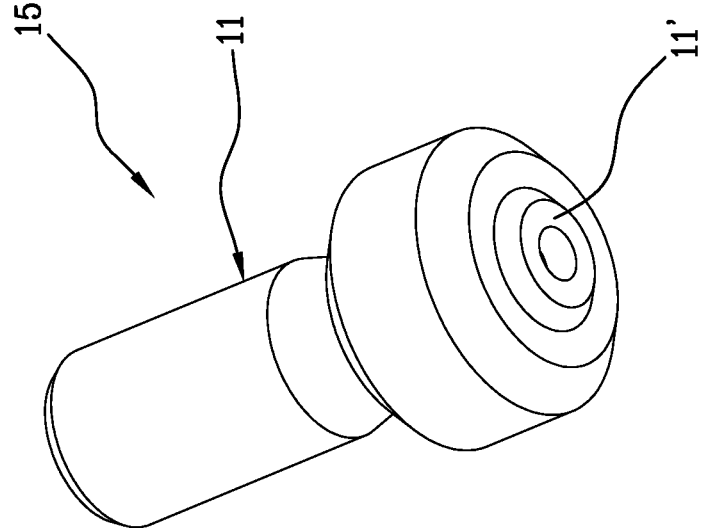
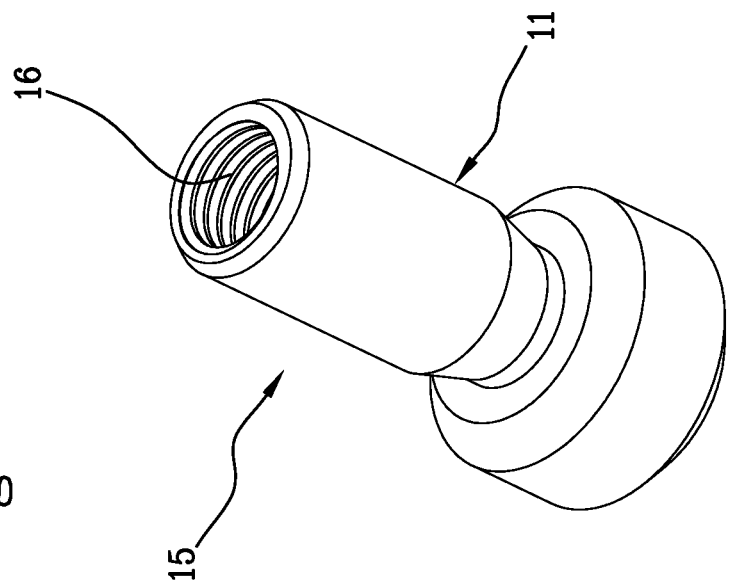

GUIDE FOR FLEXIBLE BONE DRILL AND BONE RESECTION INSTRUMENT

The present application is a National Phase Entry of PCT International Application No. PCT/IB2017/058191, which was filed on Dec. 20, 2017, and which claims priority to Application No. 102016000132039 filed in Italy on Dec. 29, 2016, the contents of which are hereby incorporated by reference.

The subject-matter of the present invention is a guide for a flexible bone drill.

Furthermore, the present invention relates to a bone resection instrument, in particular to an instrument comprising a flexible bone drill for use in arthroscopic surgery, preferably on the hip or shoulder.

However, the use of the instrument on other parts of the body is not excluded.

Such instruments are particularly useful in surgical procedures to remove pathological or congenital bony outgrowths, specifically on the hip or on the shoulder, or also during operations to fit or replace hip prostheses when preliminary cleaning of the acetabular cup is required.

Femoral acetabular conflict, or impingement, is caused by a series of congenital or acquired hip pathologies due to an imperfect conformation and abnormal contact between the parts of the hip joint (the acetabulum and the proximal part of the femur).

The femur head is normally spherical in form and articulates in a cup (acetabulum) without creating any friction or contact (impingement).

If one or both of the parts, the femur head and the acetabulum, do not fit together perfectly, this results in a condition where there is friction, known as Femoral Acetabular Impingement (FAI). A first type of femoral acetabular impingement may be due to an abnormal curvature of the femoral neck with an osteophyte on the surface surrounding the femur head, close to the neck, which interacts with and damages the acetabular lip; a second type of impingement may be caused when the acetabulum is abnormally pincer-shaped: also in this case there is interference between the neck of the femur and the lip of the acetabulum.

Femoral Acetabular Impingement is one of the most frequent causes of arthrosis of the hip joint and typically affects young adults and athletes in particular, whereas in people with a sedentary lifestyle such deformities may go unnoticed for their entire lifetime.

The worsening of this condition is due to the repeated strain that is exerted to repeatedly and forcefully perform extreme degrees of movement.

When diagnosed early the condition can be treated before the joint is compromised, improving the prognosis for patients affected by this condition.

To that end, arthroscopic surgery is performed to restore the correct femoral head-neck offset ratio by removing the bone formation on the neck.

At present, several arthroscopic instruments are used, typically motorised bone drills, which can be inserted at the site of the surgical procedure to reach the bony outgrowths to be removed at pre-set angles of entry, or which have a pre-set curvature to guide the flexible drill to the point to be operated on. However, besides involving the use of several instruments, such technique does not provide the surgeon with a high degree of flexibility when handling the drill during the operation.

Another situation that requires the removal of bony protrusions is the fitting or replacement of hip prostheses.

In the case of first-time hip replacement, when the femur is removed the concave surface of the acetabular cup is jagged and uneven and must be smoothed before fitting the prosthesis; likewise, in the case of revision surgery, after removing the old acetabular cup, which will generally have become osseointegrated with the rest over time, the acetabular surface will have osteophytes that will have caused bulging around the cup and must be removed.

Before fitting the prosthesis, not only must the acetabular seat be cleaned thoroughly to smooth its surface, but the edge of the acetabulum must also be free of any osteophytes that could make it impossible to reach the bottom of the acetabulum and prevent the correct orientation of the definitive cup.

Surgeons currently use a semi-circular bone drill with a handle that has a convex outer surface with a roughness designed to remove the bony spurs.

The bone drill is inserted into the acetabulum and manoeuvred manually to scrape the concave surface of the acetabular cup using the rough convex surface.

The Applicant has found that the bone drills of the type known in the prior art have some drawbacks associated with the excessively reduced mobility of said instrument by the surgeon during the operation, the need to use several instruments and the need to have a more flexible instrument that can be used in arthroscopic and other surgical procedures.

Therefore, the Applicant has come to the conclusion that it would be far more advantageous to be able to use a single instrument, that allows the angle of inclination to be arbitrarily defined in order to operate on the bony protrusion to be removed.

The purpose of the present invention is therefore to provide a guide for a flexible bone drill and a respective bone resection instrument, capable of overcoming the inconveniences of the prior art described above.

More precisely, the purpose of the present invention is to provide a guide for a flexible bone drill which enables said drill to be positioned easily and used effectively during a surgical procedure.

A further purpose of the present invention is to provide a bone resection instrument for removing bony protrusions in the case of femoral acetabular impingement or shoulder impingement, and for cleaning the acetabular seat when necessary in order to fit a prosthesis.

Lastly, a purpose of the present invention is to produce a bone resection instrument which allows the surgeon to have great flexibility of manoeuvre, by allowing the surgeon to adjust the angle of inclination at which the drill acts on the osteophyte during the surgical procedure, according to each patient's anatomy, while at the same time guaranteeing the utmost safety of the patient by preventing the drill from accidentally interfering with soft tissue or bone structures that must not be removed or damaged by accidentally coming into contact with the motorised instrument.

These and other aims of the invention are substantially achieved with a guide for a flexible bone drill and a bone resection instrument of the type disclosed in one or more of the following claims. The dependent claims describe some alternative embodiments of the invention.

In any case, these and further characteristics, and the respective technical advantages, will become more apparent from the description that follows of a preferred and non-exclusive embodiment of a guide for a flexible bone drill and a bone resection instrument, represented solely by way of non-limiting example.

This description is provided with reference to the accompanying figures, which are also provided solely by way of non-limiting examples, in which:

FIGS. 7a and 7b are two perspective views of a control element that is part of the guide according to the present invention.

Figure 1:
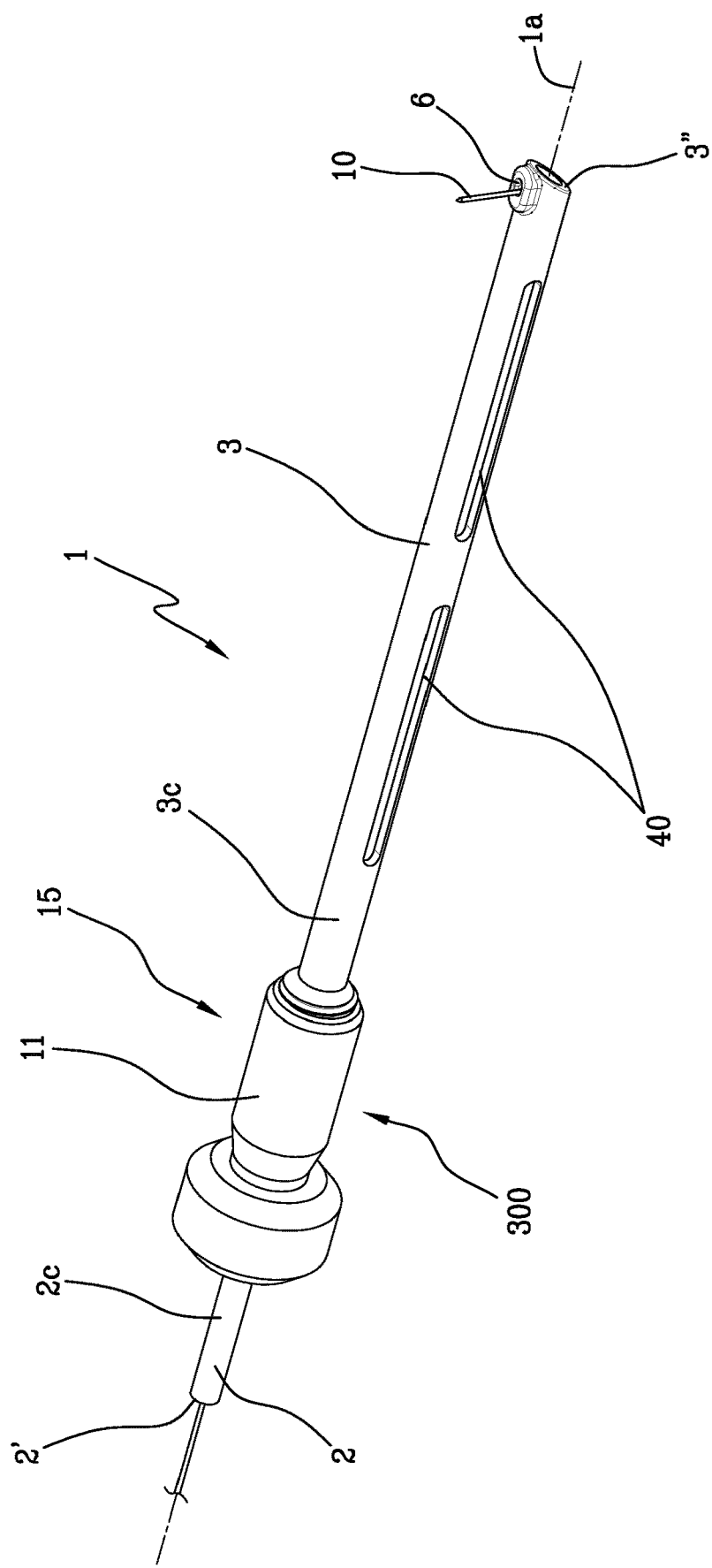
FIG. 1 is a perspective view of a guide for bone drill according to the present invention.
Figure 2:
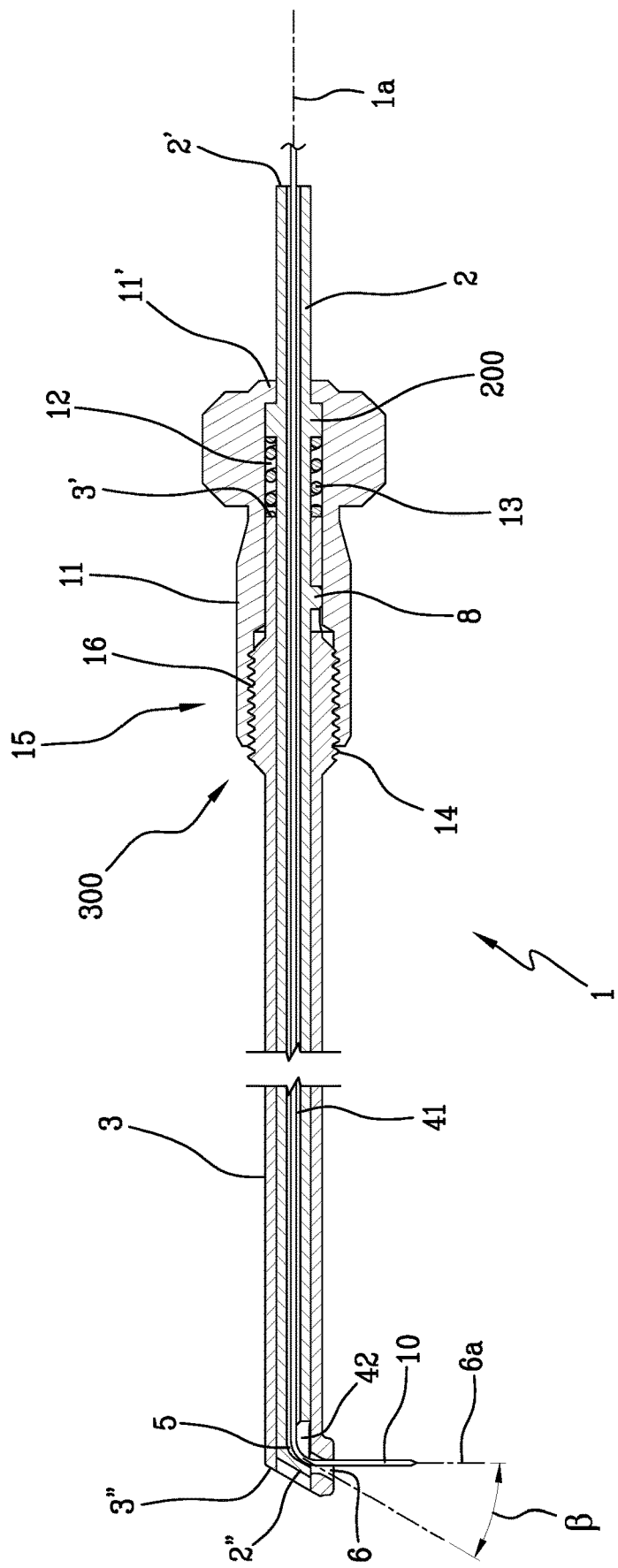
FIG. 2 is a sectioned view of a bone resection instrument comprising the guide illustrated in FIG. 1.
Figure 3:
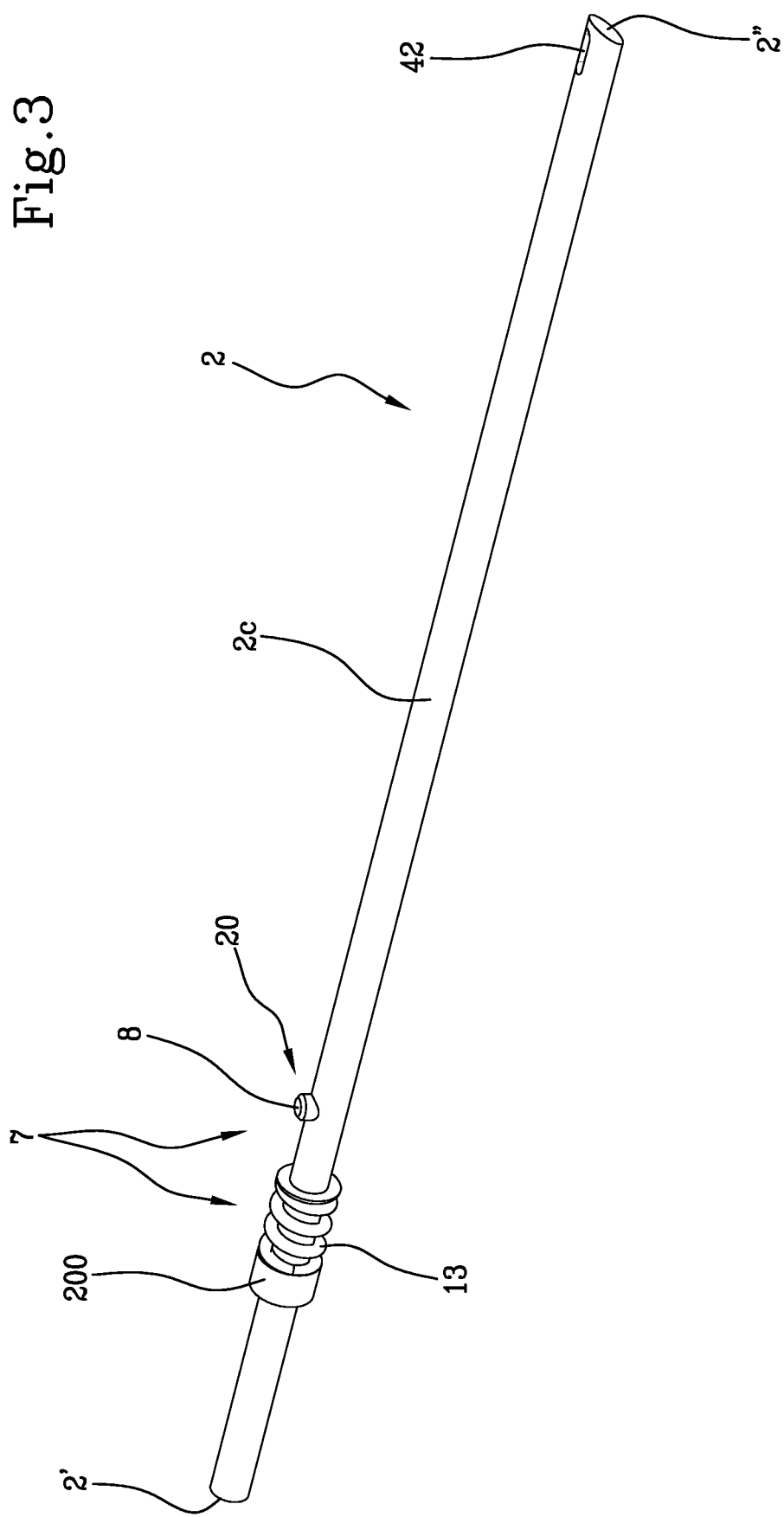
FIG. 3 is a perspective view of a first body of the guide according to the present invention.

With reference to the accompanying figures, denoted as a whole by reference numeral 1 is a guide for flexible bone drill according to the present invention.

The guide 1 comprises a first body 2 and a second body 3 which can be inserted one inside the other and are movable with respect to one another. The guide preferably extends substantially longitudinally, advantageously in the form of a cylinder, along an axis 1a.

The second body 3 is internally hollow and has an open first end 3' through which the first body 2 is inserted, and a second end 3" opposite the first end. The first body 2 also has an open first end 2' and a second end 2" opposite the first end, which is inserted into the second body 3.

The first body 2 is provided with an internal through channel 4 comprising an axial portion 41 that extends partially along a longitudinal axis 2a of the first body 2, from a first end 2' outside the second body 3, to an intermediate point 5 along the longitudinal axis 2a, and a transverse portion 42 that extends from the intermediate point 5, along the longitudinal axis 2a, towards a side wall 2c of the first body 2.

Advantageously, the transverse portion 42 is inclined at a variable angle α of between 30° and 80°, preferably between 40° and 60°, with respect to the longitudinal axis 2a of the first body 2.

The axial portion 41 and the transverse portion 42 are communicating, consecutive and in fluidic connection with the external environment.

Figure 4:
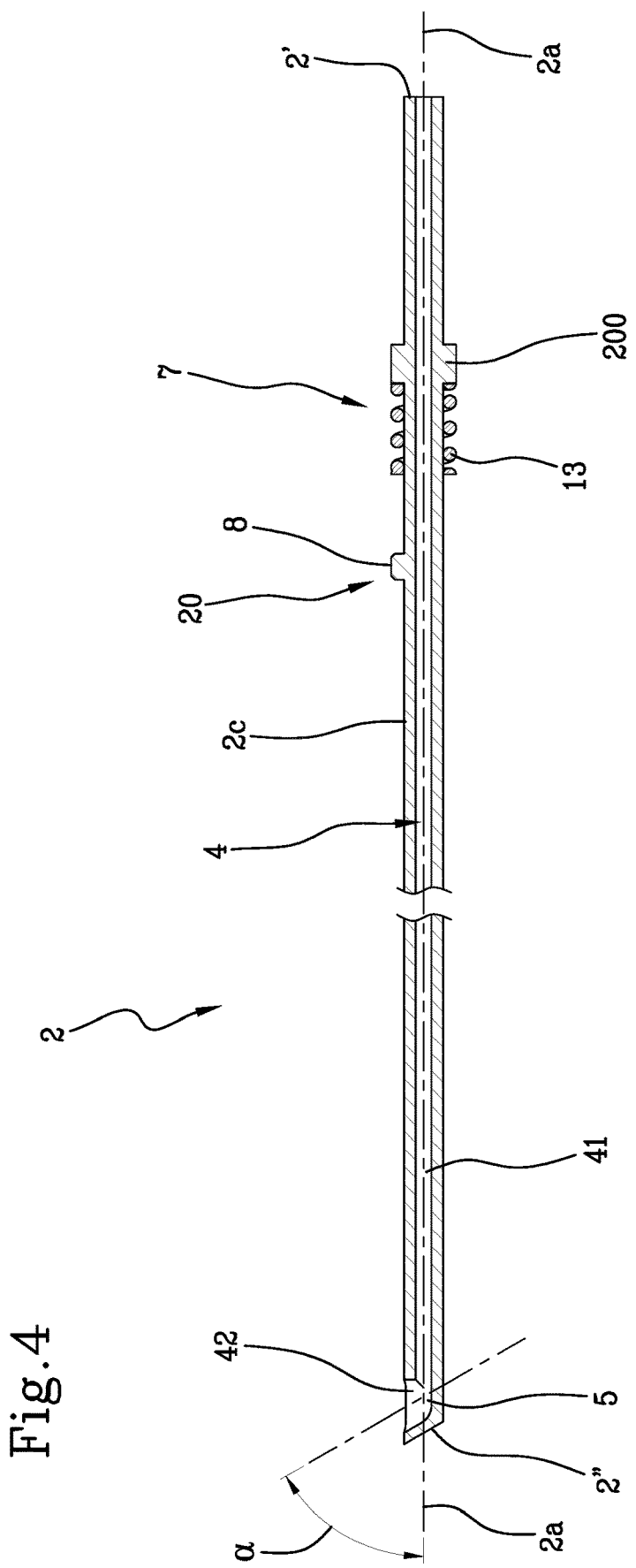
FIG. 4 is a sectioned view of the first body illustrated in FIG. 3.

As shown in FIG. 4, the axial portion 41 of the channel 4 leads to the outside through the first free end 2' of the first body 2, whereas the transverse portion 42 of the channel 4 leads to the outside from a side wall 2c of the first body 2.

The second body 3, instead, is provided with a through hole 6 in one side wall 3c that is placed in fluidic connection with the internal cavity 30; when the guide is mounted, the hole 6 is placed in fluidic connection with the through channel 4 in the first body 2.

The second body 3 may have weight-reducing slits 40 along the side wall 3c.

The first 2 and the second body 3 slide relative to one another to vary the relative position of the hole 6 in the second body 3 with respect to the through channel 4 in the first body 2.

The guide 1 cooperates with a flexible scraping element 10 to define a bone resection instrument.

Said flexible scraping instrument 10 is, preferably, a flexible bone drill suitable to be inserted into the guide 1. Advantageously, said bone drill is made, for example, of Nitinol.

Specifically, the scraping element 10 can be inserted into the channel 4 in the first body 2, from the first end 2' so as to pass through the axial portion 41 and the transverse portion 42 of the channel 4 and emerge from the second body 3 through the through hole 6.

The exit angle β of the scraping element from the guide 1 can be adjusted by adjusting the axial position of the first body 2 relative to the second body 3.

Advantageously, the exit angle β of the flexible scraping element 10 varies between 0° and 30° with respect to an axis 6a orthogonal to the longitudinal axis 1a of the guide, passing through the hole 6.

The guide 1 further comprises movement limiting means 7 suitable to limit the relative movement between the first 2 and the second 3 body both in the axial direction, to prevent the first body 2 from accidentally coming away from the second body 3, and in the rotational direction, to prevent the relative rotation of one with respect to the other about the axis of rotation 2a.

Said limiting means 7 are also capable of controlling the relative movement between the first 2 and the second 3 body both in the axial and rotational direction.

The movement limiting means 7 comprise an anti-rotation device 20 comprising a pin 8 that protrudes externally from a side wall 2c of the first body 2 and a slot 9 obtained in a side wall 3c of the second body 3.

The pin 8 is movable inside the slot 9, so as to prevent any relative rotation between the first 2 and the second 3 body.

Said device 20 in fact prevents the relative rotation, about the longitudinal axis 1a of the guide 1, of the first body 2 with respect to the second body 3, so that the hole 6 is always radially aligned with the transverse portion 42 of the channel 4, in order to prevent any deformation, undesirable bending or tearing of the scraping element 10.

Figure 5:
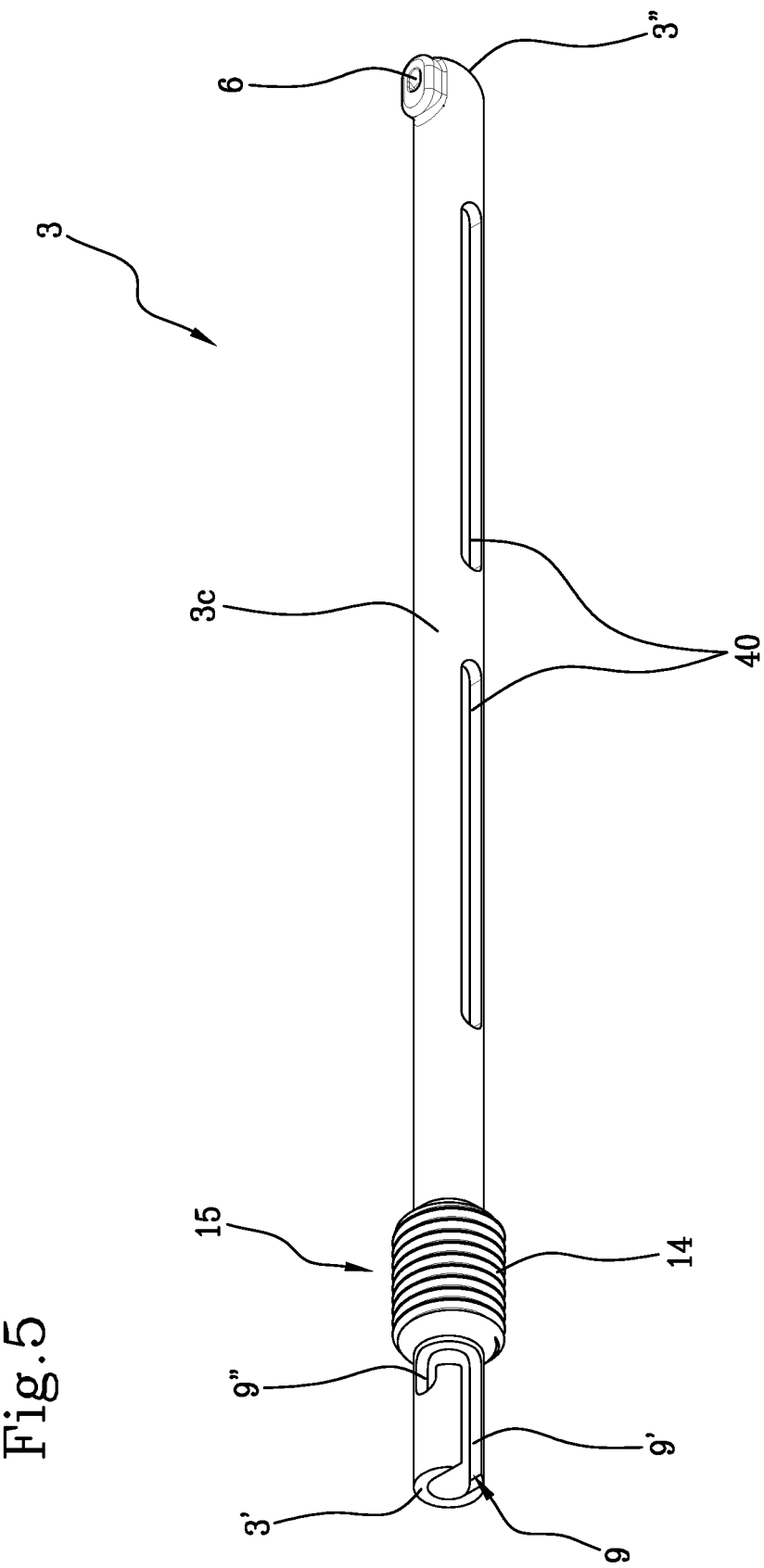
FIG. 5 is a perspective view of a second body of the guide according to the present invention.
Figure 6:
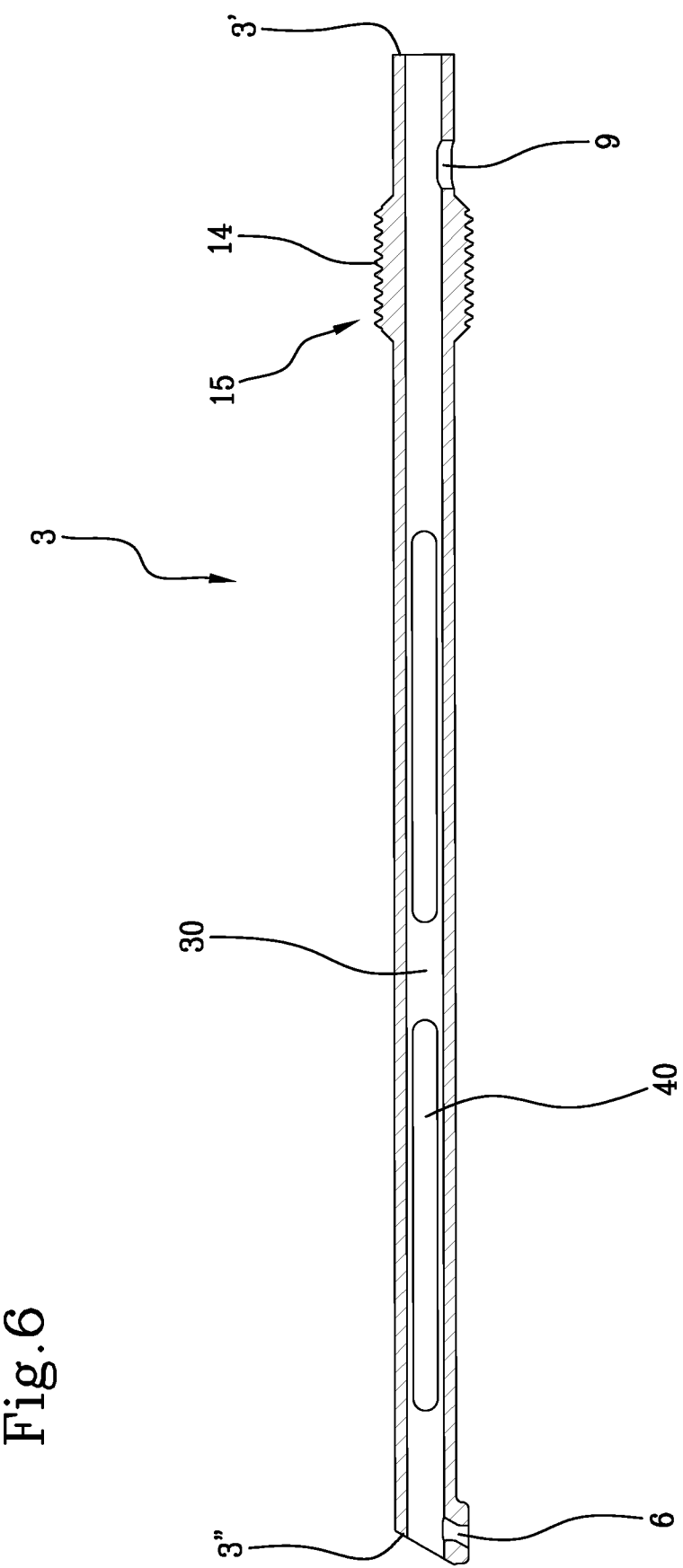
FIG. 6 is a sectioned view of the second body illustrated in FIG. 5.

The anti-rotation device 20 further defines a bayonet-type coupling to connect the first body 2 to the second body 3. As can be seen in FIG. 5, the slot 9 may, in this configuration, be hook-shaped with a first rectilinear part 9' open towards the first end 3' of the second body 3 and a second arched part 9" into which the pin 8 is inserted, in the locked position.

According to a preferred embodiment, which is not illustrated, there may be a rectilinear slot 9 closed at both ends, inside which a pin 8 is able to slide. Said movement limiting means 7 further comprise a restraint device 300 which prevents the first body 2 and the second body 3 from becoming completely detached from one another. Said restraint device 300 permits a limited relative axial translation between said two bodies.

In detail, the restraint device 300 comprises an annular flange 200 which extends radially from the first body 2.

The annular flange 200 is integral with the first annular body 2 and therefore follows its axial translatory movements.

Arranged on the outside of the first 2 and of the second 3 body there is a sleeve 11, removably constrained to the second body 3.

The annular flange 200 is movable within a housing 12 obtained inside said sleeve 11 and extending between an end portion 11' of the sleeve 11 and the first end 3' of the second body 3.

An elastic element 13, preferably a coil spring, is housed between the annular flange 200 and the first end 3' of the second body 3. Said elastic element 13 permits the controlled and limited axial travel of the first body 2 inside the second body 3, both in the compression stage, when the first body 2 is inserted into the second body 3, and in the extension stage, when the first body 2 is extracted from the second body 3.

The sleeve 11 is also part of a control device 15 the purpose of which is to operate the guide 1 and axially move the first body 2 with respect to the second body 3 in a controlled manner.

The control device 15 further comprises a first thread 14 arranged around the second body 3 and able to engage with a second internal thread 16 of the sleeve 11.

When the sleeve 11 is screwed with its thread 16 onto the thread 14 of the second body 3, it acts, via an end portion 11' thereof, on the annular flange 200, pushing the first body 2 inside the second body 3.

The annular flange 200 presses the spring 13 against the first end 3' of the second body 3: the effect of the spring 13 is to slow down and control the travel of the first body inside the second body and to facilitate the extraction of the first body 2 from the second body 3 when the sleeve 11 is operated in the opposite direction.

Simply operating the control device 15, and thus screwing or unscrewing the sleeve 11 on the second body 3, results in the relative translation of the first body 2 with respect to the second body 3.

The relative axial position between the transverse portion 42 of the channel 4 and the exit hole 6 of the second body 3 is determined, and hence the inclination of the scraping element 10 varies, depending on how far the first body 2 is inserted into the second body 3.

The invention described above achieves some important advantages.

With the guide according to the invention, the exit angle of the flexible scraper element can be adjusted simply by acting in a controlled manner on a control device in order to vary the relative axial position of the first body with respect to the second body. In this way the surgeon can operate in a precise and targeted manner at the site of the operation, to remove the bony protrusions and prepare the area to receive the new prosthesis.

The invention claimed is:

1. A guide for a flexible bone drill, comprising:
  a first body defining an internal through channel;
  a second, internally hollow body, into which said first body can be inserted;
  wherein a side wall of said second body defines a through hole suitable to be placed in fluidic connection with the internal through channel of said first body;
  wherein said internal through channel of the first body comprises:
    an axial portion, extending at least partially along a longitudinal axis of said first body, from a first free end of said first body to an intermediate point along said longitudinal axis; and
    a transverse portion, extending from said intermediate point along the longitudinal axis towards a side wall of said first body;
    wherein the flexible bone drill is insertable into the internal through channel in said first body, from the first free end of said first body so as to pass through the axial portion and the transverse portion of the internal through channel, and exit from the second body through the through hole;
  said second body and said first body being slidable relative to one another along said longitudinal axis of the first body to vary the relative position of the through hole with respect to said transverse portion of said internal through channel consequently modifying an exit angle of the flexible bone drill with respect to an orthogonal axis passing through the hole, wherein the orthogonal axis is orthogonal to a longitudinal axis of the guide, wherein the exit angle is measured between the orthogonal axis and a transverse axis that extends through the through hole and is transverse to said longitudinal axis of the first body.

2. The guide according to claim 1, wherein said transverse portion is inclined at an angle comprised between 30° and 80° with respect to the longitudinal axis of said first body.

3. The guide according to claim 2, wherein said axial portion and said transverse portion are communicating, consecutive and in fluidic connection with the external environment.

4. The guide according to claim 2, wherein said transverse portion is inclined at an angle comprised between 40° and 60° with respect to the longitudinal axis of said first body.

5. The guide according to claim 1, wherein said axial portion and said transverse portion are communicating, consecutive and in fluidic connection with the external environment.

6. The guide according to claim 5, wherein said axial portion leads to the outside through said first free end of said first body and said transverse portion leads to the outside from a side wall of said first body.

7. The guide according to claim 5, comprising a control device comprising a sleeve placed around said first and said second body, to operate said guide and axially move said first body with respect to said second body in a controlled manner.

8. The guide according to claim 1, wherein said axial portion leads to the outside through said first free end of said first body and said transverse portion leads to the outside from a side wall of said first body.

9. The guide according to claim 1, comprising:
  a movement limitor, suitable to limit and control the relative movement between said first and said second body in both the axial and rotational direction.

10. The guide according to claim 9, wherein said movement limiter comprises an anti-rotation device comprising a pin that protrudes externally from a side wall of the first body and a slot, obtained in a side wall of the second body, inside which said pin is received so as to prevent any relative rotation between the first and the second body.

11. The guide according to claim 10, wherein said anti-rotation device defines a bayonet-type coupling to connect said first body to said second body.

12. The guide according to claim 9, wherein said movement limiter comprises a restraint device that prevents the first and the second bodies from becoming completely detached from one another and permits a limited relative axial translation between said two bodies.

13. The guide according to claim 12, wherein said restraint device comprises an annular flange extending radially from the first body and movable within a housing obtained inside a sleeve arranged on the outside of said second body and connected to the latter; said housing extending between an end portion of said sleeve and the first end of said second body.

14. The guide according to claim 13, wherein said limiter comprises an elastic element arranged between said annular flange and the first end of said second body; said elastic element controlling and limiting the axial travel of the first body inside the second body and promoting a partial extraction of the first body from the second body.

15. The guide according to claim 1, comprising:
a movement limitor, suitable to limit and control the relative movement between said first and said second body in both the axial and rotational direction.

16. The guide according to claim 1, comprising a control device comprising a sleeve placed around said first and said second body, to operate said guide and axially move said first body with respect to said second body in a controlled manner.

17. The guide according to claim 16, wherein said control device further comprises a first thread arranged around said second body and able to engage with a second internal thread of said sleeve; said sleeve screwing onto the thread of the second body to move, via an end portion thereof, said first body and pushing said first body inside the second body.

18. The guide according to claim 1, comprising a control device comprising a sleeve placed around said first and said second body, to operate said guide and axially move said first body with respect to said second body in a controlled manner.

19. A bone resection instrument, comprising:
a flexible bone drill guide according to claim 1;
a flexible rotating scraping element that can be inserted in said guide;
said flexible scraping element being able to vary the exit angle from said guide according to the relative position between the first and the second body of the guide.

20. The bone resection instrument according to claim 19, wherein said exit angle of the flexible scraping element varies between 0° and 30° with respect to a central axis, orthogonal to the longitudinal axis of the guide passing through said through hole in the second body.

\* \* \* \* \*